(12) United States Patent
Muz

(10) Patent No.: US 7,740,510 B2
(45) Date of Patent: Jun. 22, 2010

(54) ELECTRODE CLAMP

(75) Inventor: Edwin Muz, Reutlingen (DE)

(73) Assignee: Nicolay Verwaltung GmbH., Nagold (DE)

( * ) Notice: Subject to any disclaimer, the term of this patent is extended or adjusted under 35 U.S.C. 154(b) by 0 days.

(21) Appl. No.: 12/289,234

(22) Filed: Oct. 23, 2008

(65) Prior Publication Data

US 2009/0062636 A1    Mar. 5, 2009

(30) Foreign Application Priority Data

Dec. 7, 2007  (DE) .................. 10 2007 059 096

(51) Int. Cl.
*H01R 4/48* (2006.01)
(52) U.S. Cl. .................. 439/759; 600/392; 439/909
(58) Field of Classification Search .............. 439/759, 439/754, 816, 819, 822, 909; 600/394
See application file for complete search history.

(56) References Cited

U.S. PATENT DOCUMENTS

| | | | | |
|---|---|---|---|---|
| 1,291,297 | A | * | 1/1919 | Walas .................. 439/829 |
| 1,294,656 | A | * | 2/1919 | Hammond .............. 439/829 |
| 4,200,348 | A | * | 4/1980 | Stupay .................. 439/269.1 |
| 4,206,960 | A | * | 6/1980 | Tantillo et al. ........... 439/593 |
| 4,220,387 | A | * | 9/1980 | Biche et al. ............. 439/470 |
| 4,674,817 | A | * | 6/1987 | Olms .................... 439/592 |
| 5,944,562 | A | * | 8/1999 | Christensson ........... 439/729 |
| 6,254,438 | B1 |   | 7/2001 | Gaunt |
| 6,487,430 | B1 | * | 11/2002 | Henderson et al. ........ 600/394 |

FOREIGN PATENT DOCUMENTS

DE        73 35 995 U1    2/1974
DE        102 25 621 B3    1/2004

* cited by examiner

*Primary Examiner*—Michael C Zarroli
(74) *Attorney, Agent, or Firm*—Roylance, Abrams, Berdo & Goodman, L.L.P.

(57) ABSTRACT

An electrode clamp (10; 100) for making contact with a film electrode and a snap electrode has a first part (12; 112), a second part (14; 114), and a contact element (60; 160). For clamping a film electrode, the two parts (12, 14; 112, 114) can be pivoted toward one another. In an initial state of the electrode clamp (10; 100), the first part (12; 112) and the second part (14; 114) have an offset (36; 136) relative to one another. The offset can be reduced by movement of the second part (14; 114) relative to the first part (12; 112) to such an extent that the snap electrode can be inserted into the electrode clamp. By a reset motion of the second part (14; 114) relative to the first part (12; 112) in the direction of the initial state, the snap electrode can be clamped against the contact element (60; 160) and contact can be made with the snap electrode. The electrode clamp (10; 100) can be connected in a mechanically detachable manner to the snap electrode.

14 Claims, 4 Drawing Sheets

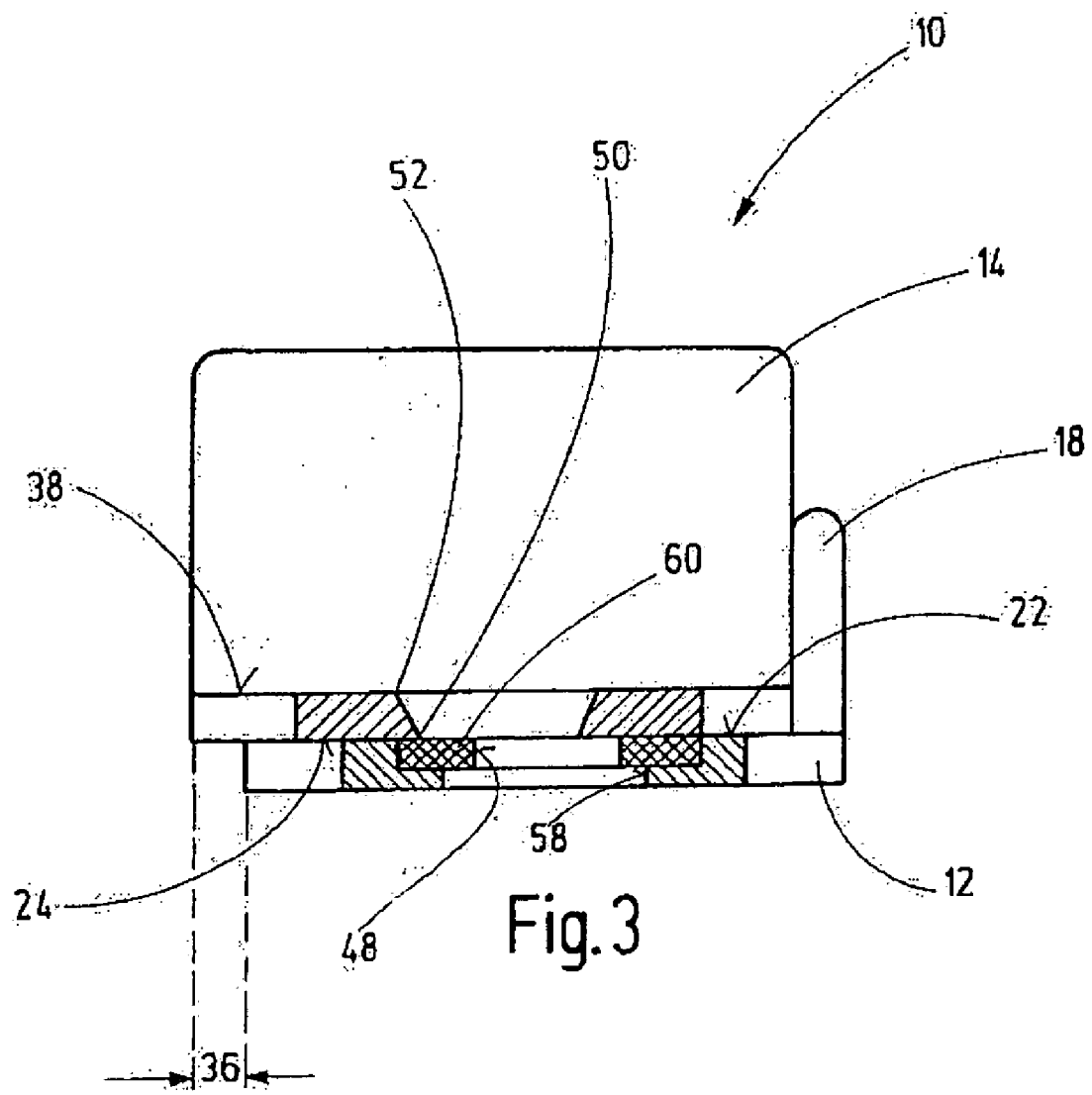

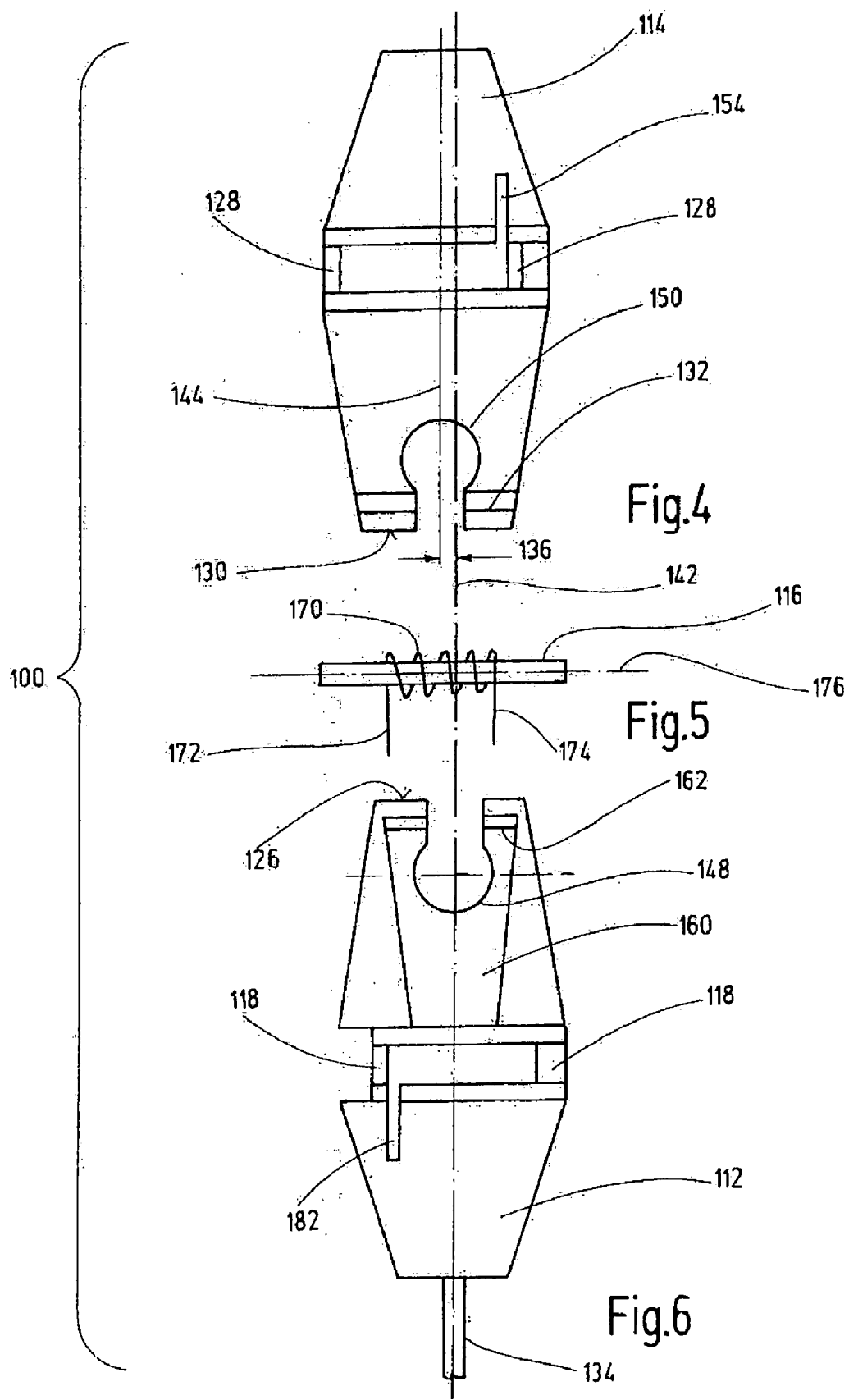

ELECTRODE CLAMP

FIELD OF THE INVENTION

The present invention relates to an electrode clamp with which both a film electrode and a snap electrode can make electrical contact.

BACKGROUND OF THE INVENTION

Electrode clamps for film and snap electrodes are disclosed in DE 102 25 621 B3 and are used, for example, in medical technology to be able to easily make contact between different electrode types there. For example, when preparing an electrocardiogram (EKG), the contact points on the body to be examined can be connected to the medical devices both via film electrodes and via snap electrodes.

SUMMARY OF THE INVENTION

An object of the present invention is to provide an improved electrode clamp improved compared to the known electrode clamp, especially one ensuring permanently reliable contact-making and simple handling.

This object is basically achieved by an electrode clamp intended mainly for use in medical technology having a first part and a second part movable relative to one another. Particularly, they can be pivoted around a pivoting axis relative to one another and can move relative to one another. Both a film electrode and a snap electrode can be mechanically clamped by the two possible relative movements and can make electrical contact by a contact element of the electrode clamp. Snap electrodes have a contact stud projecting from the electrode surface making contact with the patient for the electrode surface to be electrically connected to a medical device, for example, an electrocardiograph. Film electrodes have flat extensions of the electrode surface making contact with the patient and being able to be clamped, for example, between two flat sections of the first and second parts.

In the known clamps, the sections of the first and second parts of the electrode clamp clamping the film electrode as an alligator clip are aligned with one another in the initial position and lie congruently on top of one another. Conversely, the first and the second parts of the electrode clamp according to the present invention in the initial position have an offset which can be reduced or cancelled against the action of an energy storage mechanism located in the electrode clamp. An opening in the electrode clamp then can be cleared to receive the snap electrode such that contact is made. The snap electrode is clamped against the contact element, and contact is established by the reset motion.

In one embodiment, the first part and the contact element each have an opening through which the snap electrode can pass. The second part has a receiving space for accommodating the snap electrode at least in sections. The receiving space is bordered by a clamping means, for example, by the edge of the second part bordering the receiving space and movable into contact with the snap electrode for clamping. Clamping takes place by the interaction of the clamping means with the contact element and/or with the edge bordering the opening of the first part. For clamping and making contact, the snap electrode passing through the openings in the first part and in the contact element can be held in the receiving space of the second part at least in sections. The receiving space of the second part can likewise be bordered by an opening in the second part. The openings in the second part and in the contact element can have essentially the same contour. The opening in the first part can at least be larger in sections than the opening in the contact element. The first part is facing the electrode which can be fixed on the body to be examined.

In one embodiment, the opening of the contact element and the receiving space of the second part in the initial state of the clamp have an offset relative to one another. That offset can be reduced by a relative movement of the second part relative to the first part to such an extent that the snap electrode can be inserted into the receiving space. The snap electrode is clamped against the contact element and thus makes electrical contact by the offset which can be re-established at least partially after insertion of the snap electrode.

In one embodiment of the present invention, the relative movement of the first part and of the second part to one another takes place against the force of an energy storage mechanism. By using an energy storage mechanism there is a defined initial state of the electrode clamp because the two parts of the electrode clamp, to the extent there is no contact with an electrode, are moved by the energy storage mechanism into the initial state. In this way reliable contact-making is also ensured with one-hand operation of the electrode clamp. The energy storage mechanism can be, for example, tension/compression springs, helical springs, spiral springs or leg springs, or elastically deformable plastics.

In one embodiment, relative movement of the two parts to one another takes place such that proceeding from an initial state with offset of the openings in the second part and in the contact element, the offset is reduced or the openings are even aligned to one another by a first relative movement such that the snap electrode can be inserted into the electrode clamp.

After accommodation of the snap electrode at least in sections in the receiving space of the second part, a reset motion of the two parts takes place such that the openings after the second relative movement in turn have an offset to one another. In this way, simple mechanical fixing of the electrode clamp on the snap electrode is implemented, and in the process at the same time electrical contact is made with the snap electrode. In one embodiment, the electrode clamp after attachment to the snap electrode can be turned relative to thereto so that the desired alignment of the electrode clamp and of the associated connecting lead is possible. In one embodiment, the first and/or the second relative movement of the two parts is a linear movement. In one embodiment, the second relative movement takes place in the opposite direction to the first relative movement.

In one embodiment, the relative movement takes place laterally. The direction of movement lies in a plane defined by flat sections of the first part and of the second part used for making contact and/or clamping of film electrodes. There is no significant application of force to the patient to be examined by the lateral relative movement of the parts to one another when contact is made with the snap electrode. This leads to an increase in patient comfort, especially for patients sensitive to pain.

When contact is made with a snap electrode and a film electrode there can be a single energy storage mechanism for resetting the two parts. For example, a leg spring can store energy both in torsional deformation and also in tensile or compressive deformation. In one embodiment, there are several, in particular two energy storage mechanisms, of which one is designed for resetting of the two parts when contact is made with a snap electrode, and one for resetting the two parts when contact is made with a film electrode. In this way, the reset forces and thus the actuation forces for the two electrode types can be set separately.

In one embodiment, the snap electrode can be clamped in the opening of the contact element in that one boundary of the receiving space of the second part facing the opening adjoins the snap electrode, while at the same time the snap electrode adjoins one section of the opening of the contact element. The snap electrode is attached to the electrode clamp by clamping by an energy storage mechanism trying to increase the offset of the two parts to one another.

In one embodiment, the electrode clamp has stop means limiting the relative movement of the two parts to one another. Interacting stop means on the first and second parts determine a first stop position, in particular an initial state, in which external forces do not act on the electrode clamp, and in which the openings in the contact element and in the second part have such an offset that a snap electrode cannot be inserted into the electrode clamp. In this initial state, however, a film electrode can be clamped and can make contact, for example, by the two parts being able to pivot as an alligator clip and being able hold a film electrode between themselves. In particular, the surfaces of the two parts which face each other in spite of the offset of the two parts have sufficient overlapping so that a film electrode can be clamped reliably between at least parts of the facing surfaces of the first and second parts.

Other interacting stop means on the first and second part determine a second stop position in which the two parts can be moved so far against one another and against the force of the energy storage mechanism that a snap electrode can be inserted through the opening in the first part and in the contact element into the receiving space of the second part. In one embodiment, in the second stop position, the openings in the contact element and in the second part are aligned to one another, in particular, are completely aligned or congruent to one another.

In one embodiment, the stop means are each formed in one piece by the first and/or second part which can be molded articles of an electrically insulating material, in particular a polymer plastic.

In one embodiment, the openings for the snap electrode in the first part and in the contact element are formed by a through opening or a hole. Preferably, the openings are formed in the flat section of the first part and of the contact element. The opening in the first part can, for example, be formed in the clamp tip of the first part for making contact with the film electrode. The opening is open toward the edge bordering the first part, in particular the flat section of the first part, i.e., the opening does not have a closed edge boundary. The corresponding applies to the receiving space of the second part. In this way it is possible to place the electrode clamp on the snap electrode either from overhead, or alternatively, and in many applications preferably, to bring the electrode clamp from the side to the snap electrode and to insert the snap electrode into the second section of the opening over the first section which is open toward the end.

In one embodiment, in the first section of the opening forming the connection toward the edge, the inside width is less than in the second section which is at a distance from the edge. In one embodiment, the second section is analogous at least partially to the shape of the snap electrode, in particular, it is made circular in sections.

In one embodiment, the first section toward the edge is bordered by two edges extending parallel at least in sections. In one embodiment, a first section near the edge widens toward its edge-side end. This configuration simplifies the insertion of the snap electrode.

In one embodiment, the lateral relative movement of the two parts for making contact with the snap electrode is parallel to or even along an axis forming a pivoting axis for a pivoting motion of the two parts relative to one another for making contact with a film electrode. In one embodiment, the axis forms the guide means for the lateral relative movement.

The axis can be formed by an elongated and at least sectionally cylindrical body. Alternatively, the axis can also be defined by some other shape and can enable pivoting of the two parts relative to one another, for example, by guidance of the second part taking place in a bearing drum of the first part without an elongated cylindrical axis body being necessary.

In one embodiment, the pivoting axis is pivoted in bearing brackets of one of the two parts of the electrode clamp. Preferably, the bearing brackets are formed in one piece from the first and/or second part. In one embodiment, the bearing brackets of the pivoting axis in the first part of the electrode clamp together with the corresponding bearing brackets in the second part of the electrode clamp form stop means for limiting the lateral relative movement of the two parts.

In one embodiment, only one of the two parts has an electrical contact element for making contact both with the film electrode and the snap electrode, preferably on that part on which the connecting lead of the electrode clamp is also fixed. In one embodiment, the contact element is flat and preferably formed by a metal sheet. In particular, the contact element can be a punched part. The contact element can be produced as a shaped part from metal and can have a thickness from 0.1 mm to 1 mm, preferably 0.2 mm to 0.5 mm, and in particular approximately 0.3 mm.

In one embodiment, the first part in the forward flat region designed for making contact with film and snap electrodes has a thickness from 0.2 mm to 2 mm, preferably from 0.4 mm to 1.2 mm, and in particular a thickness of approximately 0.8 mm.

In one embodiment, the contact element has a clamping means for clamping the film electrode. In one embodiment, the clamping means is formed by the contact element having point, linear or polygon-shaped elevations relative to its otherwise flat progression at one or more positions. In one embodiment, the elevations of the contact element are formed by deforming an originally flat contact element by bending or embossing or punching or a combination of those working processes. In one embodiment, the clamping means is located in one section of the contact element lying over the first section of the opening of the first part, which section is near the edge.

In one embodiment, the flat section of the part opposite the part having the contact element has a recess corresponding to the clamping means. In particular, for a strip-shaped clamping means, a corresponding groove-shaped recess is provided. In this way a film electrode inserted between the two parts is molded over the strip of the contact element and into the corresponding recess. Unintentional withdrawal of the electrode clamp from the film electrode is then effectively prevented by the required forces which have been greatly increased by this measure.

In one embodiment, the contact element has an opening analogous to the opening of the first part of the electrode clamp at least in sections. In particular, the opening of the contact element can also have a first section near the edge and a second section at a distance from the edge. Preferably, the inside width in the second section of the contact element is larger than in the first section. In the second section, the opening of the contact element is shaped such that a snap electrode inserted into the opening of the first part can be moved against the contact element to make electrical contact. The inside width in the second section of the contact element can be smaller for this purpose than the inside width in the second section of the opening of the first part. The electrode clamp, in addition to high reliability, also affords contact protection and simple handling.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure:

FIG. 3 is an elevational view in section of the embodiment of FIG. 2 taken along line of FIG. 2;

FIG. 4 is a bottom plan view of a second part of an electrode clamp according to a second exemplary embodiment of the present invention;

FIG. 5 is a top plan view of the arrangement of the energy storage mechanism and one axis of the second embodiment of FIG. 4;

FIG. 6 is a top plan view of a first part of the electrode clamp of the second embodiment of FIGS. 4 and 5;

DETAILED DESCRIPTION OF THE INVENTION

Figure 1:
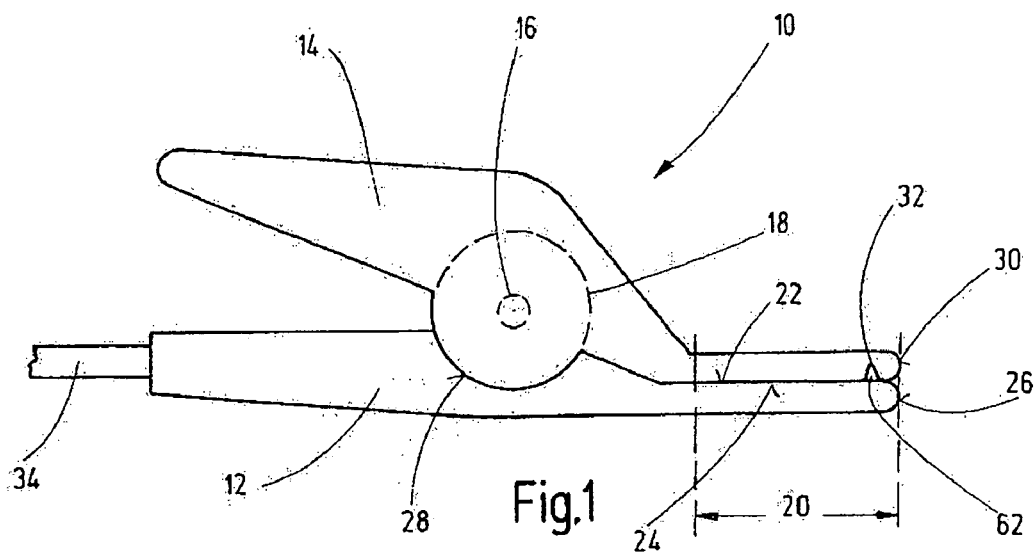
FIG. 1 is a side elevational view of an electrode clamp according to a first exemplary embodiment of the present invention.

FIG. 1 shows a side view of a first embodiment of an electrode clamp 10 according to the present invention, in which the first part 12 can be movably connected to the second part 14 via an axis 16. The axis 16 can be fixed in the first part 12 or in the second part 14. In this embodiment, the axis 16 is pressed into a bearing bracket 28 formed preferably in one piece from the second part 14 and is pivotally connected to a bearing bracket 18 formed preferably in one piece from the first part 12. In this way, both pivoting or rocking of the second part 14 relative to the first part 12 around the axis 16, as well as lateral displacement motion of the two parts 12, 14 in the direction of the axis 16, are possible.

In the front region 20, the electrode clamp 10 has a first surface 22 formed from first part 12 and a second surface 24 formed from the second part 14, which surfaces in the initial state of the electrode clamp 10 shown in FIG. 1 extend parallel to one another. Between surfaces 22, 24 a film electrode (not shown) can be clamped. The surfaces 22 and 24 on their free ends each have an edge 26, 30. The second part 14, in the frond region 20 and near the edge 30, has a recess 32. The clamping means or member 62 of the first part 12 engages recess 32. A film electrode placed between the surfaces 22 and 24 of the electrode clamp 10 can then be clamped such that unintentional pulling of the electrode clamp 10 away from the film electrode is effectively prevented. The electrode which has made contact with the electrode clamp 10 can be connected to a medical device via the connecting lead 34 of the electrode clamp 10.

To make contact with a film electrode, the second part 14 can be pivoted against the action of an energy storage mechanism around the axis 16 relative to the first part 12 so that the film electrode can be inserted between the two surfaces 22, 24. The film electrode can be mechanically clamped, and electrical contact can be made when the second part is pivoted back.

The bearing bracket 18 of the first part of the electrode clamp 10, shown by the broken line in FIG. 1, is located approximately in the middle relative to the longitudinal extension of the first part 12 and has a contour which is circular at least in sections. The circular contbur has a center point coinciding with the center of the axis 16.

The bearing bracket 28 is located essentially in the middle with reference to the longitudinal extension of the second part 14. In its lower section facing the first part 12, bearing bracket 28 has a circular outside contour with a center coinciding with that of the axis 16. In particular, in one advantageous configuration the circular sections of the bearing brackets 18, 28 can have the same diameter.

Figure 2:
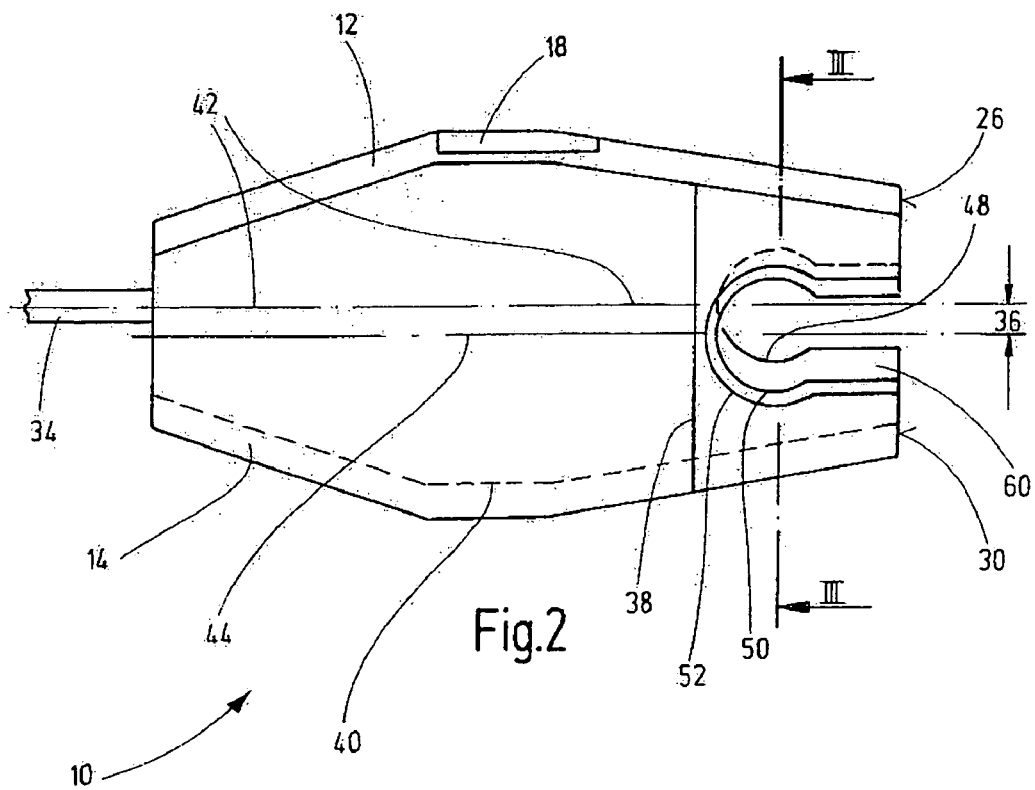
FIG. 2 is a top plan view of the embodiment of FIG. 1.

FIG. 2 shows a plan view of the embodiment of FIG. 1 with a lateral offset 36 of the second part 14 relative to the first part 12 in the initial state of the electrode clamp 10. The lateral edge of the second part 14 then projects beyond the lateral edge 40 of the first part 12 by the offset 36. The contour of the first part 12 is essentially symmetrical to the center line 42 of the first part 12. The contour of the second part 14 is essentially symmetrical to the center line 44 of the second part 14. The center lines 42, 44 in the illustrated embodiment have an offset 36. Proceeding from the first ends of the two parts 12, 14 adjacent to the connecting lead 34, the contours of the first part 12 and of the second part 14 widen in the direction of the edges 26, 30 on the opposite second ends, first trapezoidally to the center section of the first and second parts 12 and 14 in which the axis 16 (FIG. 1) is located.

In the middle section, each contour runs essentially parallel to the center lines 42 and 44. The contours then taper trapezoidally as far as the edges 26 and 30 of the first part 12 and of the second part 14. The length of the trapezoidal section on the first end is approximately 20 to 50% of the longitudinal extension of the first part 12 and of the second part 14. The length of each trapezoidal section on the second end is approximately 40 to 70% of the longitudinal extension of the first part 12 and of the second part 14. The length of each middle section extending parallel to the center lines 42 and 44 is approximately 10 to 30% of the longitudinal extension of the first part 12 and of the second part 14.

In the forward region 20 (see FIG. 1) bordered by the deflection line 38 of the second part 14 in the direction of the connecting lead 34 in the first part 12, an opening 58 (FIG. 3) is arranged symmetrically to the center line 42 of the first part 12. Opening 58 is intended for routing through or inserting a snap electrode into the electrode clamp 10. The contact element 60 has a corresponding opening 48 also located symmetrically to the center line 42. In the second part 14, a receiving space for the snap electrode is bordered in the illustrated embodiment by an opening 50. The opening 50 within the second part 14 extends beveled to the outer opening edge 52 in the second part 14.

The opening 58 of the first part 12 and the opening 48 of the contact element 60 are open toward the edge 26 bordering the flat section of the first part 12 and has a first section near the edge bordered by edges extending parallel at least in sections and parallel to the center line 42 of the first part 12. Adjoining the first section, the opening 58 of the first part 12 and the opening 48 of the contact element 60 have a second, pitch circle-shaped section in which the snap electrode can be accommodated.

The opening 50 of the second part 14 is open toward the edge 30 bordering the flat section of the second part 14 and has a first section near the edge and bordered by edges extending parallel at least in sections and parallel to the center line 44 of the first part 14. Adjoining the first section, the opening 50 has a second, pitch circle-shaped section in which the snap electrode can be accommodated.

In the initial state shown in FIG. 2, the two openings 48, 50 of the contact element 60 and of the second part 14 have an offset 36. In this embodiment, the offset is sized such that the snap electrode cannot be inserted into the electrode clamp 10. To make contact with the snap electrode, the second part 14 can be moved laterally relative to the first part 12 and relative to the contact element 60 fixed on the first part 12 until the offset 36 is reduced or the openings 48, 50 are even essentially congruent. In this state the snap electrode can be inserted either directly into the second, pitch circle-shaped sections of the openings 48, 50 of the contact element and of the second part, or the snap electrode can be inserted into the pitch circle-shaped sections of openings 48, 50 laterally over the first sections of the openings 48, 50 of the contact element and of the second part.

The displacement of the second part 14 necessary to reduce the offset 36 relative to the first part 12 takes place against the force or biasing of the energy storage mechanism located in the electrode clamp 10. The energy stored in the energy storage mechanism after insertion of the snap electrode into the openings 48 and 50 results in a resetting motion of the second part 14 relative to the first part 12. In this way, clamping contact of the second part 14 with the snap electrode occurs, in particular pressing of the snap electrode against the contact element 60 of the electrode clamp 10. The contact element 60 also extends into the front region 20 of the electrode clamp 10 and in the embodiment is also located on the surface 22 of the first part 12. The contact element 60 is set back relative to the edge 26 of the first part 12 in a shock-proof manner.

FIG. 3 shows a section through the embodiment as shown in III-III of FIG. 2. The contact element 60 is used both to make contact with the film electrode and to make contact with a snap electrode. When contact is made with the film electrode, the surface 24 of the second part 14 in the illustrated forward region 20 of the electrode clamp 10 presses against the surface 22 of the first part. A film electrode inserted between these two surfaces 22 and 24 is accordingly conductively connected to the contact element 60. The opening 50 of the second part 14 widens in the direction to the end opposite the first part 12. This improves contact-making and clamping of the snap electrode having on its free end a partially spherical or curved section.

The bearing bracket 18 of the first part 12 extends over a height of approximately 30 to 60% of the overall height of the electrode clamp 10. The bearing bracket 18 of the first part 12 is at least partially accommodated in the recess of the second part 14 when the offset 36 is reduced between the first part 12 and the second part 14. When the offset 36 has been adequately reduced, the openings 48 and 50 are aligned to one another to such an extent that insertion of the snap electrode into the electrode clamp 10 is possible. The opening 58 of the first part 12 has a somewhat greater width than the opening 48 of the contact element 60 so that when the snap electrode is clamped, reliable contact-making by the contact element 60 is ensured.

FIGS. 4, 5, and 6 show components of a second exemplary embodiment of an electrode clamp 100 according to the present invention. FIG. 4 shows a view of the second part 114 of the second embodiment from underneath. The center line 142 of the first part 112 extends over all three figures for purposes of representation of the lateral relative location of the components in the initial state of the electrode clamp 100. FIG. 5 shows a plan view of an arrangement of the energy storage mechanism 170 and the axis 116 of the second embodiment. FIG. 6 shows a plan view of the first part 112 of the second embodiment.

Extending parallel to the edge 130 of the second part 114, a recess 132 interacts with the clamp strip 162 of the contact element 160 to ensure mechanically reliable fixing of the film electrode in the electrode clamp 100. The first part 112 relative to the second part 114 has an offset 136.

The axis 116, around which the second part 114 can be pivoted relative to the first part 112, extends in the axis direction 176 extending at a right angle to the center line 142. An energy storage mechanism 170 causing a resetting motion both for lateral displacement and for pivoting of the two parts 112, 114 is made as a leg spring. The spring has a first leg 172 assigned to the first part 112, and a second leg 174 assigned to the second part 114. In the second part 114, adjacent to one of the bearing brackets 128, a recess 154 receives the second leg 174. The second leg 174 is moved in the axial direction 176 together with the second part 114 when the second part 114 moves laterally. In this way stretching or compression of the energy storage mechanism 170 is caused by this movement.

The contact element 160, on its side adjacent to the edge 126, has a clamp strip 162 made, for example, as an impression into the contact element 160, and forming an elevation projecting out of the plane of the contact element 160 in the direction of the second part 114. By interaction with the recess 132 of the second part 114, a film electrode can be clamped in a mechanically stable manner between the clamp strip 162 and the recess 132. To ensure a sufficiently shock-proof electrode clamp 100, the edge of the contact element 160 adjacent to the edge 126 of the first part 112 is set back relative to the latter so that touching of the edges 126 by the user of the electrode clamp 100 does not result in touching of the contact element 160.

The axis 116 is pivoted in the bearing brackets 118 of the first part 112. The second leg 172 of the energy storage mechanism 170 can be accommodated in the recess 182 adjacent to the bearing bracket 118 of the first part 112. The bearing bracket 118 of the first part 112 on the left in FIG. 6 is offset to the inside by the offset 136 of the left outside edge of the first part 112. The other bearing bracket 118 is located flush on the right outside edge of the first part 112. The bearing bracket 128 of the second part 114 on the right in FIG. 4 is offset to the inside by the offset 136 of the right outside edge of the second part 114. The other bearing bracket 128 is located flush on the left outside edge of the second part 114. When the first part 112 and the second part 114 lie on top of and aligned with one another without an offset, i.e., when the offset 136 disappears completely, the bearing brackets 128 of the second part 114 adjacent to the bearing brackets 118 of the first part 112 adjoin one another. In this way, the relative movement of the two parts 112 and 114 to one another, for reduction of the offset 136 is limited, and the bearing brackets 118, 128 are used here as stop means or stops.

The connecting lead 134 is connected electroconductively to the contact element 160. For this purpose, the contact element on its end near the connecting lead 134 is shaped appropriately. The electroconductive connection can take place, for example, by crimping, soldering or clamping. Alternatively, insulation piercing connection of the connecting lead 134 to the contact element 160 constitutes an economical connection method.

Figure 7:
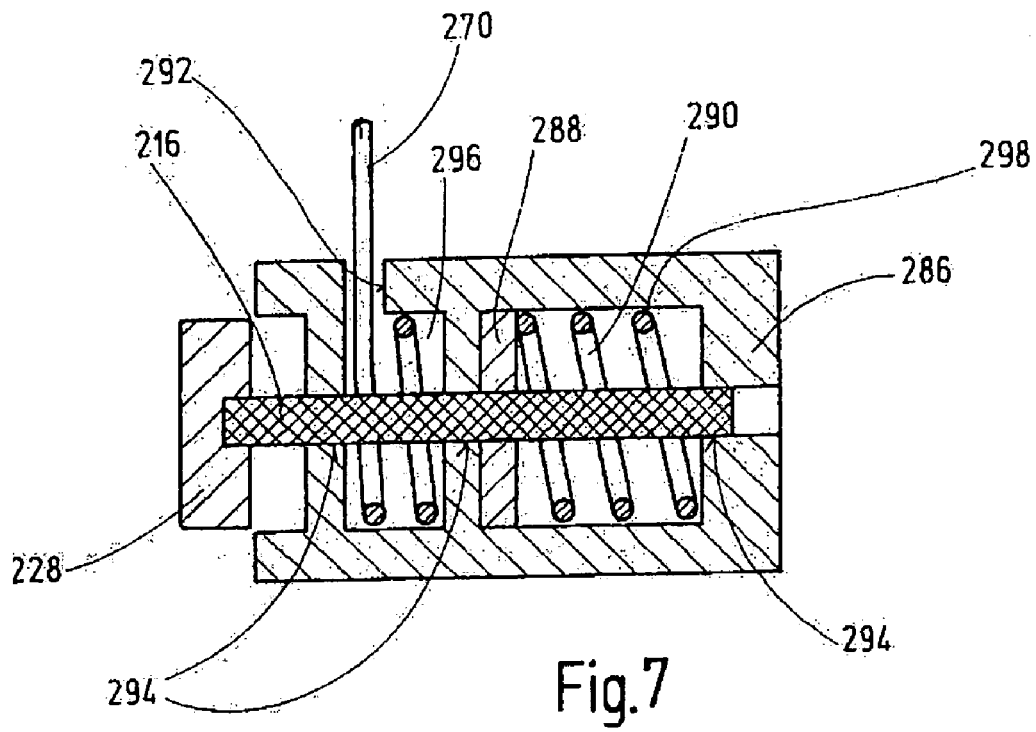
FIG. 7 is a front elevational view in section of an arrangement of an energy storage mechanism and one axis of an electrode clamp according to a third exemplary embodiment of the present invention.

FIG. 7 shows partially in a section an arrangement of energy storage mechanisms 270, 290 and the axis 216 of a third exemplary embodiment of the present invention. A bearing drum 286 formed preferably in one piece by the first part of the electrode clamp according to the present invention has bearing bushes 294 in which an axis or axle 216 is guided. One end of axis 216 is provided with a bearing bracket 228 formed preferably in one piece from the second part of the electrode clamp according to the present invention. A disk 288 is permanently connected to the axis 216. The energy storage mechanism 290 in the second chamber 298 of the bearing drum 286 has one end adjoining the inside surface of the bearing drum 286 and its other end adjoining the disk 288. In the illustrated initial state the energy storage mechanism 290 applies a force to the disk 288 and thus effects the extended state of the bearing bracket 228, so that there is an offset 136 (see FIG. 4) between the first and the second part of the electrode clamp according to the present invention.

To reduce the offset, the bearing bracket 228 and the second part of the electrode clamp can be moved relative to the first part and relative to the bearing drum 286 such that the bearing bracket 228 moves in the direction of the bearing drum 286. After insertion of a snap electrode into the electrode clamp, the energy storage mechanism 290, by its attempt to expand again or its biasing, will move the disk 288 and the axis 216 as well as the bearing bracket 228 back in the direction of the initial position and to ensure mechanically secure fixing and electronic contact-making of the snap electrode.

In a first chamber 296 of the bearing drum 286, there is another energy storage mechanism 270 in which one leg emerges through the exit opening 292 out of the bearing drum 286. The energy storage mechanism 270 is supported with its leg emerging from the bearing drum 286 on the second part of the electrode clamp and is used here, in particular, to produce a contact pressure for making contact with the film electrode.

Figure 8:
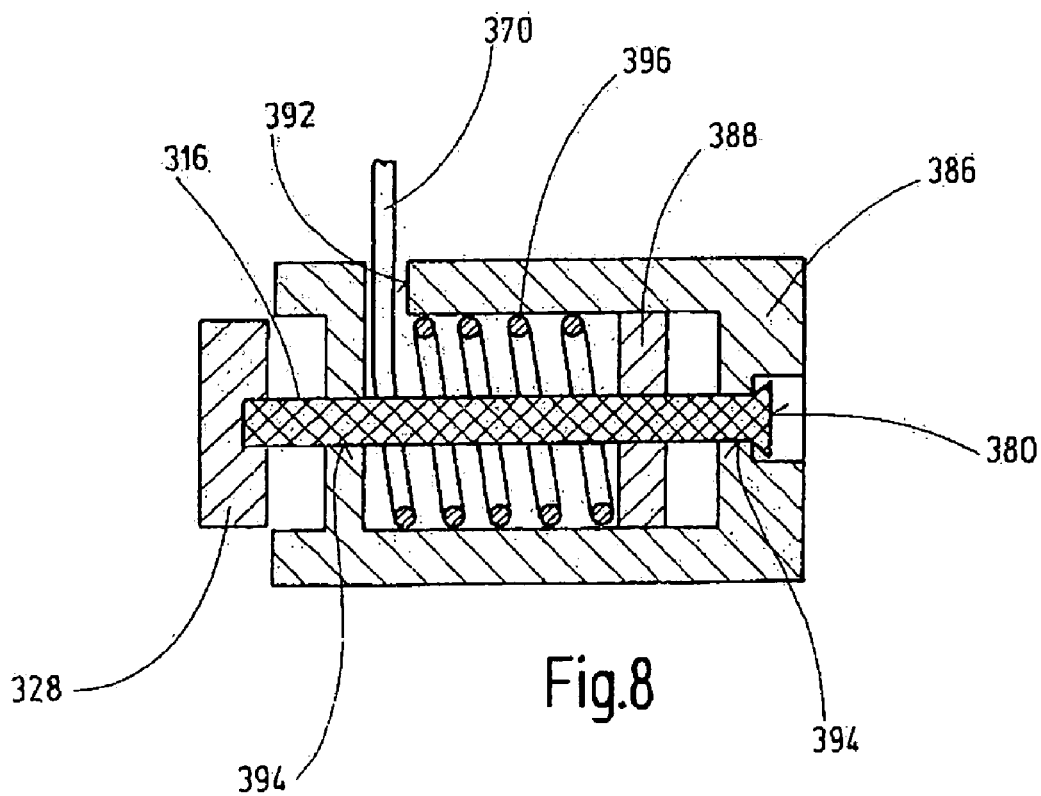
FIG. 8 is a front elevational view in section of an arrangement of an energy storage mechanism and one axis of an electrode clamp according to a fourth exemplary embodiment of the present invention.

FIG. 8 shows partially in a section an arrangement of an energy storage mechanism 370 and an axis or axle 316 of a fourth embodiment. The bearing drum 386 is preferably formed in one piece from the first part of the electrode clamp according to the present invention, while the bearing bracket 328 is formed preferably in one piece from the second part of the electrode clamp. The bearing bracket 386 is penetrated by the axis 316. The axis 316 is guided in the bearing bushes 394 of the bearing drum 386. The axis 316 is connected at one of its ends permanently to its bearing bracket 328. On its other end, it is provided with a stop 380, for example, produced by simple compression of the axis on this end and interacting with the adjacent bearing bush 394 such that the mobility of the bearing bracket 328 out of the drum 386 is limited. Further movement of the bearing bracket 328 in this direction is not possible as soon as the stop 380 adjoins the bearing bush 394.

A disk 388 is permanently connected to the axis 316 and is permanently connected to the end of an energy storage mechanism 370 located in the first chamber 396 of the bearing drum 386. This end of energy storage mechanism 370 is adjacent to the disk 388, so that movement of the bearing bracket 328 in the direction of the bearing drum 386 leads to expansion of the energy storage mechanism 370. This movement of the bearing bracket 328 is caused by a reduction of the offset 136 of the two parts of the electrode clamp. One leg of the energy storage mechanism 370 is guided to emerge from the bearing drum 386 through an exit opening 392 and acts on the second part of the electrode clamp. In the initial state of the electrode clamp, that leg leads to the surfaces 22, 24 pressing on one another in the forward region 20 of the electrode clamp and to contact being made with a film electrode.

While various embodiments have been chosen to illustrate the invention, it will be understood by those skilled in the art that various changes and modifications can be made therein without departing from the scope of the invention as defined in the appended claims.

What is claimed is:

1. An electrode clamp for making contact with a film electrode having flat extensions extending from a patient contacting surface and a snap electrode having a contact stud projecting from a patient contacting surface, comprising:
   a first part having a contact element thereof; and
   a second part pivotally coupled to said first part for pivotal movement about a pivotal axis between an open position for receiving a film electrode therebetween and a closed position detachably clamping the film electrode therebetween and against said contact element, said first and second parts being in a first state where said first and second parts have an offset relative to one another, being relatively movable to reduce said offset in a second state allowing a snap electrode to be inserted in said first and second parts, and being resettable to said first state clamping the snap electrode against said contact element for electrical contact therebetween and in a mechanically detachable manner.

2. An electrode clamp according to claim 1 wherein said first and second parts are movable translationally between said first state and said second state relative to facing surfaces thereon.

3. An electrode clamp according to claim 2 wherein said first and second parts are movable laterally between said first and second states.

4. An electrode clamp according to claim 1 wherein at least one of said parts has a stop limiting relative movement of said first and second parts between said first and second states.

5. An electrode clamp according to claim 1 wherein said contact element has an opening for receiving the snap electrode; and
said second part has a receiving space for accommodating at least a portion of the snap electrode.

6. An electrode clamp according to claim 5 wherein said opening is a through opening in a flat region of said contact element, and is open to a free edge of a border of said first part.

7. An electrode clamp according to claim 6 wherein said opening has a first section near said free edge and a second section spaced a distance from said free edge, said first section having a smaller inside width than said second section.

8. An electrode clamp according to claim 5 wherein said opening has a first section near a free edge of said first part and a second section spaced a distance from said free edge, said first section having a smaller inside width than said second section.

9. An electrode clamp according to claim 5 wherein said opening is located in a section of said contact element in which the film electrode is clamped.

10. An electrode clamp according to claim 1 wherein said first and second parts are relatively movable between the first and second states along said pivot axis.

11. An electrode clamp according to claim 1 wherein said contact element is only on said first part.

12. An electrode clamp according to claim 1 wherein said contact element comprises a clamp for clamping the film electrode.

13. An electrode clamp according to claim 1 wherein an energy storage mechanism provides a biasing force opposing relative movement of said first and second parts from the first state to the second state and provides a clamping force on the contact element against the snap electrode.

14. An electrode clamp according to claim 1 wherein said first and second parts are movable between said first and second states independently of the pivotal movement thereof between said open and closed positions.

* * * * *